United States Patent
Crimmin et al.

Patent Number: 5,821,262
Date of Patent: Oct. 13, 1998

[54] HYDROXAMIC ACID DERIVATIVES AS INHIBITORS OF CYTOKINE PRODUCTION

[75] Inventors: Michael John Crimmin; Raymond Paul Beckett, both of Oxford, United Kingdom

[73] Assignee: British Biotech Pharmaceuticals Limited, Oxford, England

[21] Appl. No.: 615,184

[22] PCT Filed: Oct. 4, 1994

[86] PCT No.: PCT/GB94/02145

§ 371 Date: Oct. 28, 1996

§ 102(e) Date: Oct. 28, 1996

[87] PCT Pub. No.: WO95/09841

PCT Pub. Date: Apr. 13, 1995

[30] Foreign Application Priority Data

Oct. 7, 1993 [GB] United Kingdom ............... 9320660

[51] Int. Cl.$^6$ ............ C07D 333/34; C07C 323/60; C07C 317/44; A61K 31/16
[52] U.S. Cl. ............ 514/445; 514/575; 549/62; 562/621; 562/623
[58] Field of Search .................... 514/575, 397, 514/399, 419, 445; 562/621, 623; 548/315.1, 335.1, 335.5, 494, 495; 549/62

[56] References Cited

U.S. PATENT DOCUMENTS

| | | | |
|---|---|---|---|
| 4,996,358 | 2/1991 | Handa et al. | 562/621 |
| 5,300,501 | 4/1994 | Porter et al. | 514/238.2 |
| 5,300,674 | 4/1994 | Crimmin et al. | 560/42 |
| 5,310,763 | 5/1994 | Campion et al. | 514/575 |

*Primary Examiner*—Mukund J. Shah
*Assistant Examiner*—Deepak R. Rao
*Attorney, Agent, or Firm*—Banner & Witcoff, Ltd

[57] ABSTRACT

A compound of formula (I):

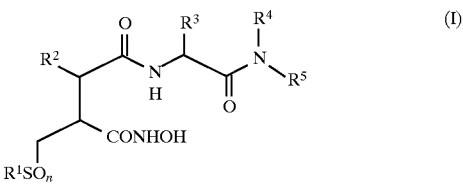

wherein:
$R^1$ represents a $(C_1-C_6)$alkyl, phenyl, substituted phenyl, or heterocyclyl group; $R^2$ represents a $(C_1-C_6)$alkyl group; $R^3$ represents:
  (I) the side chain of arginine, lysine, tryptophan, histidine, serine, threonine, or cysteine, in which any polar amino, hydroxy, mercapto, guanidyl, imidazolyl or indolyl group is rendered substantially nonpolar by substitution at the polar N-, O- or S-atom; or
  (ii) the side chain of aspartic or glutamic acid, in which side chain the carboxylic acid group is amidated;
$R^4$ represents hydrogen or a $(C_1-C_6)$alkyl or phenyl $(C_1-C_6)$alkyl group; $R^5$ represents hydrogen or and n is 0, 1 or 2; or substituted phenyl groups; or a salt solvate or hydrate thereof. Compositions containing compound (I) and methods for treatment of diseases or conditions mediated by TNF or MMPs in mammals.

15 Claims, No Drawings

HYDROXAMIC ACID DERIVATIVES AS INHIBITORS OF CYTOKINE PRODUCTION

This application is a 371 of PCT/GB94/02145 filed Oct. 4, 1994.

This invention relates to therapeutically active hydroxamic acid derivatives, to processes for their preparation, to pharmaceutical compositions containing them, and to the use of such compounds in medicine. In particular, the compounds are inhibitors of the release of tumour necrosis factor (TNF) from cells, and inhibitors of metalloproteinases involved in tissue degradation.

TNF is a cytokine which is produced initially as a cell-associated 28 kD precursor. It is released as an active, 17 kD form (Jue, D-M et al., (1990) Biochemistry 29:8371–8377), which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Preventing the production or action of TNF is, therefore, predicted to be a potent therapeutic strategy for many inflammatory, infectious, immunological or malignant diseases. These include, but are not restricted to, septic shock, haemodynamic shock and sepsis syndrome (Mathison et al. (1988) J. Clin. Invest. 81:1925–1937; Miethke et al. (1992) J. Exp. Med. 175:91–98), post ischaemic reperfusion injury, malaria (Grau et al., (1989) Immunol. Rev. 112:49–70); mycobacterial infection (Barnes et al. (1992) Infect. Imm. 60:1441–6), meningitis, psoriasis, congestive heart failure, fibrotic disease, cachexia, graft rejection, cancer, autoimmune disease, inflammatory bowel disease (eg Crohn's disease), rheumatoid arthritis, multiple sclerosis, radiation damage, toxicity following administration of immunosuppressive monoclonal antibodies such as OKT3 or CAMPATH-1 and hyperoxic alveolar injury.

Current clinical anti-TNF strategies involve the use of corticosteroids such as dexamethasone, and the use of cyclosporin-A or FK506, which are non-specific inhibitors of cytokine gene transcription. Phosphodiesterase inhibitors such as pentoxyfilline have been shown to be more specific inhibitors of TNF gene transcription (Endres S et al. (1991) Immunol. 72:56–60, Schandene et al. (1992) Immunol. 76:30–34, Alegre M L, et al. (1991); Transplantation 52:674–679, Bianco et al. (1991) Blood 78:1205–1211). Thalidomide has also been shown to inhibit TNF production by leucocytes (Sampajo et al, (1991) J. Exp. Med. 173:699–703). In experimental settings, anti-TNF monoclonal antibodies, soluble TNF receptors and soluble TNF receptor/immunoadhesins have been shown to specifically inhibit the effects of TNF action (Bagby et al. (1991) J. Infect. Dis. 163:83–88, Charpentier et al. (1991) Pressemed. 20:2009–2011, Silva et al. (1990) J. Infect. Dis. 162:421–427; Franks et al. (1991) Infect. Immun. 59:2609–2614, Tracey et al. (1987) Nature 330:662–664; Fischer et al. (1992) PNAS USA in press, Lesslauer et al. (1991) Eur. J. Immunol. 21:2883–2886, Ashkenazi et al. (1991) PNAS USA 88:10535–10539)

It has recently been shown that the effects of TNF are mediated by two peptides, TNFα and TNFβ. Although these peptides have only 30% homology with each other, they activate the same receptors and are encoded by immediately adjacent genes. As used herein, the term tumour necrosis factor or TNF therefore means tumour necrosis factor α and peptides having a high degree of sequence homology with, or substantially similar physiological effects to, TNFα, for example TNFβ.

It is an object of the present invention to provide compounds which substantially inhibit the release of TNF from cells, and therefore may be used in the treatment of conditions mediated by TNF. Such uses include, but are not limited to, the treatment of inflammation, fever, cardiovascular effects, haemorrhage, coagulation and acute phase response, cachexia and anorexia, acute infections, shock states, graft versus host reactions and autoimmune disease.

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis or invasion. Several classes of MMP inhibitors have been proposed, including derivatives of hydroxamic acid. The following patent publications disclose hydroxamic acid-based MMP inhibitors, but disclose nothing concerning inhibition of TNF release:

U.S. Pat. No. 4,599,361 (Searle)
EP-A-0231081 (ICI)
EP-A-0236872 (Roche)
EP-A-0274453 (Bellon)
WO 90/05716 (British Bio-technology)
WO 90/05719 (British Bio-technology)
WO 91/02716 (British Bio-technology)
WO 92/09563 (Glycomed)
U.S. Pat. No. 5,183,900 (Glycomed)
EP-A-0497192 (Roche)
WO 92/13831 (British Bio-technology)
WO 92/17460 (SmithKline Beecham)
EP-A-0489577 (Celltech)
EP-A-0489579 (Celltech)
WO 92/22523 (Research Corporation Technologies)
WO 93/09090 (Yamanouchi)
WO 93/09097 (Sankyo)

The MMP inhibiting hydroxamic acid derivatives disclosed in those publications can be regarded as having the following basic structure (IA):

$$\text{(IA)}$$

wherein the five substituents $R_1$–$R_5$ may vary according to the detailed disclosure of each publication. For compounds falling within the broad categories disclosed in those publications, the balance of intrinsic level of activity, degree of specificity of activity for a particular category of MMP, and pharmacokinetic properties can vary in an unpredictable way as the substituents $R_1$–$R_5$ are varied. Their intrinsic potency against particular MMPs can be high. For example, many have a collagenase $IC_{50}$ by the in vitro test method of Cawston and Barrett, (Anal. Biochem., 99, 340–345, 1979) of less than 50 nM. Unfortunately, however, many of the specific compounds disclosed in those publications have poor water solubility, leading to severe formulation difficulties, and/or have generally poor pharmacokinetic properties. Identifying hydroxamic acid-based MMP inhibitors having a good balance of high intrinsic activity, good water solubility and acceptable pharmacokinetic properties, such that the compounds are easy to formulate and have high in vivo activity in the target disease or condition, remains a much sought after goal in the art.

It is a further object of this invention to provide compounds which, in addition to inhibiting TNF release, also inhibit the action of MMPs, and therefore may be used in the treatment of patients who suffer from conditions mediated by TNF and/or MMPs.

It is also an object of the invention to provide compounds having acceptable water solubility and an acceptable pharmacokinetic profile.

WO-A-90 05719 (British Bio-technology). mentioned above, discloses compounds of general formula

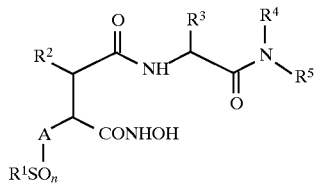

where $R^1$ represents hydrogen or an alkyl, phenyl, thienyl, substituted phenyl, phenylalkyl, heterocyclyl, alkylcarbonyl, phenacyl or substituted phenacyl group; or, when n=0, $R^1$ represents $SR^x$ wherein $R^x$ represents a group

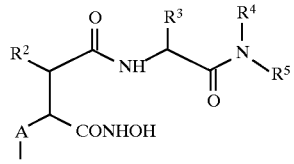

$R^2$ represents a hydrogen atom or an alkyl, alkenyl, phenylalkyl, cycloalkylalkyl or cycloalkenylalkyl group, $R^3$ represents an amino acid residue with R or S stereochemistry or an alkyl, benzyl, ($C_1$–$C_6$ alkoxy) benzyl or benzyloxy ($C_1$–$C_6$ alkyl) group; $R^4$ represents a hydrogen atom or an alkyl group; $R^5$ represents a hydrogen atom or a methyl group; n is an integer having the value 0, 1 or 2; and A represents a hydrocarbon chain optionally substituted with one or more alkyl, phenyl, or substituted phenyl groups, and their salts and N-oxides. In WO-A-90 05719 such compounds are disclosed as having collagenase inhibitory activity, with consequent utility in the management of diseases involving tissue degradation and/or the promotion of wound healing.

The compounds of the present invention differ in structure from those of WO-A-9005719 principally in the identity of the substituent $R^3$. In the compounds generically disclosed in WO-A-9005719, $R^3$ is an amino acid side chain or a ($C_1$–$C_6$)alkyl, benzyl, ($C_1$–$C_6$)alkoxybenzyl, benzyloxy ($C_1$–$C_6$)alkyl or benzyloxybenzyl group. However, compounds in which $R^3$ is the side chain of an amino acid which contains a polar substituent, such as an amino, carboxyl, hydroxy, mercapto, guanidyl, or indolyl substituent, are not specifically exemplified or their properties specifically characterised in WO-A-9005719. In the compounds of the present invention, $R^3$ represents an amino acid side chain carrying a derivatised polar substituent, as is explained further below.

According to the present invention there is provided a compound of formula (I):

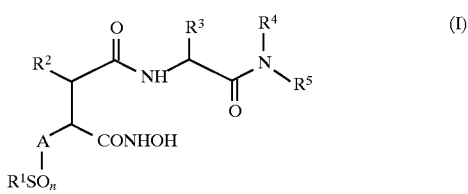

wherein:
$R^1$ represents hydrogen or an ($C_1$–$C_6$)alkyl, ($C_1$–$C_6$) alkoxycarbonyl($C_1$–$C_6$)alkyl, phenyl, substituted phenyl, phenyl ($C_1$–$C_6$)alkyl, heterocyclyl, ($C_1$–$C_6$) alkylcarbonyl, phenacyl or substituted phenacyl group;

$R^2$ represents hydrogen or a ($C_1$–$C_6$)alkyl, ($C_2$–$C_6$) alkenyl, phenyl ($C_1$–$C_6$)alkyl, cycloalkyl ($C_1$–$C_6$)alkyl or cycloalkenyl ($C_1$–$C_6$)alkyl group;

$R^3$ represents the characteristic side chain of a natural amino acid which naturally carries a polar amino, hydroxy, mercapto, guanidyl, imidazolyl or indolyl group in the said side chain, in which any such polar group is optionally N-, O- or S-substituted, or $R^3$ represents the characteristic side chain of a natural amino acid which naturally carries a polar carboxylic acid group in the said side chain, in which such carboxylic acid group is amidated;

$R^4$ represents hydrogen or a ($C_1$–$C_6$)alkyl or phenyl ($C_1$–$C_6$)alkyl group;

$R^5$ represents hydrogen or a methyl group;

n is 0, 1 or 2;

and A represents a ($C_1$–$C_6$)hydrocarbon chain optionally substituted with one or more ($C_1$–$C_6$)alkyl, phenyl, or substituted phenyl groups;

or a salt solvate or hydrate thereof.

In the compounds of this invention, the substituents $R^1$ are in general the same as those known in the corresponding position of the compounds disclosed in WO 90/05719; the substituents $R^2$ are in general the same as those known in the corresponding position of the compounds disclosed in U.S. Pat. No. 4,599,361, WO 90/05719, EP-A-0489577 and EP-A-0489579; and the substituents $R^4$ and $R^5$ are in general the same as those known in the corresponding position of the compounds disclosed in WO 90/05719.

As used herein the term "$C_1$–$C_6$ alkyl" or "saturated hydrocarbon chain of up to 6 C atoms" refers to a straight or branched chain alkyl moiety having from 1 to 6 carbon atoms, including for example, methyl, ethyl, propyl, isopropyl, n-, iso, sec and 1-butyl, pentyl and hexyl.

The term "$C_2$–$C_6$ alkenyl" or "unsaturated hydrocarbon chain of up to 6 C atoms" refers to a straight or branched chain alkenyl moiety having from 2 to 6 carbon atoms and having in addition one double bond of either E or Z stereochemistry where applicable. This term would include, for example, vinyl, 1-propenyl, 1- and 2-butenyl and 2-methyl-2-propenyl.

The term "cycloalkyl" refers to a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" refers to an unsaturated alicyclic moiety having from 3–8 carbon atoms and includes, for example, cyclohexenyl, cyclooctenyl, cycloheptenyl, cyclopentenyl, cyclobutenyl and cyclopropenyl. In the case of cycloalkenyl rings of from 5–8 carbon atoms, the ring may contain more than one double bond.

The term "heterocyclyl" or "heterocyclic" refers to a 5–7 membered heterocyclic ring containing one or more heteroatoms selected from S, N and O, and optionally fused to a benzene ring, including for example, pyrrolyl, furanyl, thienyl, imidazolyl, oxazolyl, thiazolyl, pyrazolyl, pyridinyl, pyrrolidinyl, pyrimidinyl, morpholinyl, piperizinyl, indolyl and benzimidazole.

Unless otherwise specified in the context in which it occurs, the term "substituted phenyl" or "substituted phenacyl" means phenyl or phenacyl in which the phenyl ring is substituted with up to four substituents, each of which independently may be $C_1$–$C_6$ alkoxy, hydroxy, thio, $C_1$–$C_6$ alkylthio, amino, halo (including fluoro, chloro, bromo and iodo), trifluoromethyl, nitro, —COOH, —$CONH_2$ or —$CONHR^A$ wherein $R^A$ is a $C_1$–$C_6$ alkyl group or the residue of a natural alpha-amino acid.

The term "characteristic side chain of a natural amino acid which naturally carries a polar amino, hydroxy, mercapto, guanidyl, imidazolyl or indolyl group in the said side chain" means the characteristic side chain attached to the —CH($NH_2$)(COOH) moiety in the following amino acids: arginine, lysine, tryptophan, histidine, serine, threonine, tyrosine, and cysteine. When $R_3$ in the compounds of the invention is one of those side chains, the polar substituent may optionally be N-, O- or S-substituted.

The term "N-, O- or S-substituted" when used in relation to a polar group in a side chain of a natural alpha-amino acid means a derivative of such a group which is rendered substantially non-polar by substitution at the polar N- O- or S-atom. In this context:

N-substituted amino groups include groups of formula —$NR_6R_7$ wherein $R_6$ represents $C_1$–$C_6$ alkyl, phenyl ($C_1$–$C_6$ alkyl), formyl, ($C_1$–$C_6$ alkyl)C(=O)— (eg acetyl), ($C_1$–$C_6$ alkyl)$SO_2$—, phenyl$SO_2$—, (($C_1$–$C_6$ alkyl) phenyl)$SO_2$—, ($C_1$–$C_6$ alkyl)SO—, (($C_1$–$C_6$ alkyl)phenyl)SO—, ($C_1$–$C_6$ alkyl)$_2$P(=O)— and ($C_1$–$C_6$ alkyl)C(=O)O—, phenyl ($C_1$–$C_6$ alkyl)C(=O)O—, and $R_7$ represents hydrogen, $C_1$–$C_6$ alkyl, or phenyl($C_1$–$C_6$ alkyl);

O-substituted hydroxy groups include ($C_1$–$C_6$ alkyl) ethers and silyl ethers, or phenyl($C_1$–$C_6$ alkyl)ethers and silyl ethers, and acyloxy groups such as acetoxy;

S-substituted mercapto groups include sulphides, disulphides, sulphoxides and sulphones, for example ($C_1$–$C_6$ alkyl)sulphanyl, sulphinyl and sulphonyl groups, and phenyl($C_1$–$C_6$ alkyl)sulphanyl, sulphinyl and sulphonyl groups, as well as acylthio groups such as acetylthio;

N-substituted imidazolyl, indolyl or guanidyl groups include $C_1$–$C_6$ alkyl and phenyl($C_1$–$C_6$ alkyl)O($C_1$–$C_6$ alkyl)—such as benzyloxymethyl derivatives, carbamates such as t-butoxycarbonyl and benzyloxycarbonyl derivatives, and in the case of the guanidyl group. N-nitro and mesitylene sulphonyl derivatives.

However, these are only examples of the many N-, O- and S-substituted derivatives known in the art, and others will be known to the skilled person.

The term "characteristic side chain of a natural amino acid which naturally carries a polar carboxylic acid group in the said side chain" means the characteristic side chain attached to the —CH($NH_2$)(COOH) moiety in the amino acids aspartic and glutamic acid. $R_3$ in the compounds of the invention may be an amidated derivative of one of those side chains.

Examples include those notionally derived from amines of formula $HNR_8R_9$, wherein $R_8$ and $R_9$ independently represents $C_1$–$C_6$ alkyl, or phenyl($C_1$–$C_6$ alkyl).

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom adjacent the —CONHOH moiety—S,

C atom adjacent the $R^2$ group—R,

C atom adjacent the $R_3$ group—S, but mixtures in which the above configurations predominate are also contemplated.

Presently preferred compounds of the invention include those in which, independently or in any combination:

$R^1$ represents hydrogen or an ($C_1$–$C_6$)alkyl, phenyl, thienyl, benzyl, acetyl, phenacyl or substituted phenyl, for example 4-hydroxy-, 4-amino- or 4-methoxyphenyl group;

$R^2$ represents a ($C_3$–$C_6$)alkyl group, for example an iso-butyl group;

$R^3$ represents the characteristic side chain of a natural amino acid which naturally carries a polar amino group, in which the said amino group is substituted by ($C_1$–$C_6$ alkyl)C(=O)—, or ($C_1$–$C_6$ alkyl)C(=O)O—, the ($C_1$–$C_6$alkyl) moiety being for example a methyl or tert-butyl group.;

$R^4$ represents a ($C_1$–$C_4$)alkyl group;

$R^5$ represents a hydrogen atom;

n is 0 or 2;

A is —$CH_2$—;

or salts solvates or hydrates thereof.

Specific compounds of the invention are:

$N^2$-[4-(N-Hydroxyamino)-3S-(4-hydroxyphenylthiomethyl)-2R-isobutylsuccinyl]-$N^6$-tert-butyloxycarbonyl-L-lysine-$N^1$-methylamide $N^2$-[4-(N-Hydroxyamino)-3S-(4-hydroxyphenylthiomethyl)-2R-isobutylsuccinyl]-$N^6$-tert-butyloxycarbonyl-$N^6$-(4-hydroxyphenylthiomethyl)-L-lysine-$N^1$-methylamide $N^2$-[4-(N-hydroxyamino)-3S-(2-thienythiomethyl)-2R-isobutylsuccinyl]-$N^6$-tert-butyloxycarbonyl-L-lysine-$N^1$-methylamide)

$N^2$-[4-(N-Hydroxyamino)-3S-(4-hydroxyphenylthiomethyl)-2R-isobutylsuccinyl]-O-tert-butyl-L-threonine-$N^1$-methylamide $N^2$-[4-(N-Hydroxyamino)-3S-(4-hydroxyphenylthiomethyl)-2R-isobutylsuccinyl]-L-glutamine-$N^1$,$N^5$-dimethylamide $N^2$-[4-(N-Hydroxyamino)-3S-(4-hydroxyphenylsulphonylmethyl)-2R-isobutylsuccinyl]-$N^6$-acetyl-L-lysine-$N^1$-methylamide and salts, hydrates and solvates thereof.

A compound of the invention which is presently particularly preferred, inter alia for its potency in inhibiting TNF release, and its water solubility is:

$N^2$-[4-(N-Hydroxyamino)-3S-(4-hydroxyphenylthiomethyl)-2R-isobutylsuccinyl]-$N^6$-acetyl-L-lysine-$N^1$-methylamide and salts (for example the hydrochloride), hydrates and solvates thereof.

Compounds of general formula (I) may be prepared by any suitable method known in the art and/or by the following process, which itself forms part of the invention, namely a process for preparing a compound of general formula (I) as defined above, comprising:

(a) coupling an acid of general formula (II)

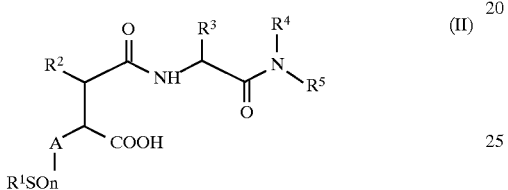

or an activated derivative thereof with hydroxylamine, O-protected hydroxylamine, or a salt thereof, $R^1$, $R^2$, $R^3$, $R^4$, $R^5$, A and n being as defined in general formula (I) except that any substituents in $R^1$, $R^2$, $R^3$, and A which are potentially reactive with hydroxylamine, O-protected hydroxylamine or their salts may themselves be protected from such reaction, then removing any protecting groups from the resultant hydroxamic acid moiety and from any protected substituents in $R^1$, $R^2$, $R^3$ and A or (b) optionally after step (a) converting a compound of general formula (I) into another compound of general formula (I).

Compounds of general formula (I) which are sulphoxides or sulphones can be prepared from sulphanyl compounds of general formula (I) (n=0) by oxidation.

Conversion of (II) to an activated intermediate such as the pentafluorophenyl, hydroxysuccinyl, or hydroxybenztriazyl ester may be effected by reaction with the appropriate alcohol in the presence of a dehydrating agent such as dicyclohexyl dicarbodiimide (DCC), N,N-dimethylaminopropyl-N-ethyl carbodiimide (WSCDI), or 2-ethoxy-1-ethoxycarbonyl-1,2-dihydroquinoline (EEDQ). Esterification of (IIA) may be effected by standard methods.

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl, t-butyldimethylsilyl, tetrahydropyranyl or benzyl ether, or as readily cleavable esters such as the acetate. Carboxy groups are often protectable as readily cleavable esters, such as the t-butyl or benzyl ester.

A compound of formula (II) may be prepared by de-esterification (such as by hydrolysis) of an ester of formula (IV)

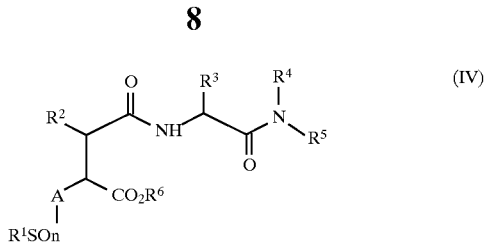

wherein $R^1$, $R^2$, $R^3$, $R^4$, $R^5$, A and n are as defined in general formula (I) and $R^6$ represents $C_1$–$C_6$ alkyl, 2-trimethylsilylethyl, phenyl $C_1$–$C_6$ alkyl or substituted phenyl $C_1$–$C_6$ alkyl.

A compound of formula (IV) can be prepared from an ester of formula (V) or an acid of formula (VI)

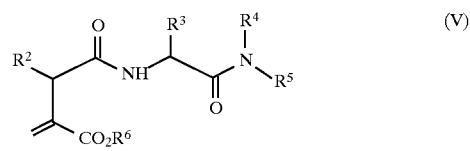

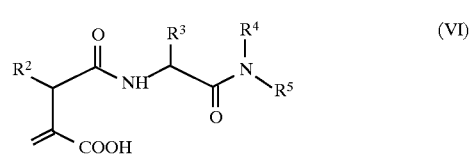

wherein $R^2$, $R^3$, $R^4$, and $R^5$, are as defined in general formula (I) and $R^6$ represents $C_1$–$C_6$ alkyl, phenyl $C_1$–$C_6$ alkyl or substituted phenyl $C_1$–$C_6$ alkyl, by reaction with a thiol $R^1SH$, wherein $R^1$ is as defined in formula (I), to give compounds wherein A represents a methylene group, or by reaction with a cuprate of formula $(R^1\text{—S-}A^1)_2CuLi$ wherein $R^1$ is as defined in formula (I), and $A^1$ is such that $-A^1\text{-}CH_2$— is identical to -A- as defined in formula (I).

Esters of formula (V) can be prepared by esterifying acids of formula (VI) with an appropriate alcohol $R^6OH$ or other esterifying agent.

An acid of formula (VI) can be prepared by reacting a malonic acid derivative of formula (VII)

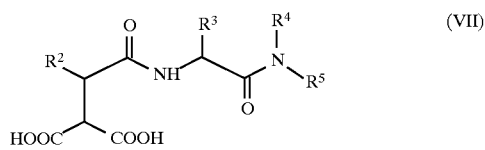

wherein $R^2$, $R^3$, $R^4$, and $R^5$, are as defined in general formula (I), with formaldehyde in the presence of piperidine.

An acid of general formula (VII) can in turn be prepared by de-esterifying (for example by hydrolysis) a compound of formula (VIII)

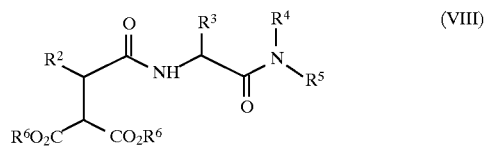

wherein $R^2$, $R^3$, $R^4$, and $R^5$ are as defined in general formula (I) and $R^6$ represents $C_1$–$C_6$ alkyl, phenyl $C_1$–$C_6$ alkyl or substituted phenyl $C_1$–$C_6$ alkyl.

A compound of general formula (VIII) can be prepared by coupling a compound of formula (IX) with a compound of formula (X)

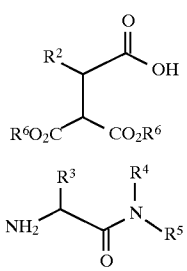

(IX)

(X)

wherein $R^2$, $R^3$, $R^4$, and $R^5$ are as defined in general formula (I) and $R^6$ represents $C_1$–$C_6$ alkyl, phenyl $C_1$–$C_6$ alkyl or substituted phenyl $C_1$–$C_6$ alkyl.

The starting materials and other reagents are either available commercially or can be synthesised by simple chemical procedures.

For example, a substituted acid of formula (IX) may be prepared by reacting an ester of formula (XI)

(XI)

wherein Y represents halo and $R^2$ and $R^6$ are as defined above, with a malonate derivative of formula (XII)

$$R^6O_2C\frown CO_2R^6 \quad (XII)$$

wherein $R^6$ is as defined above, with the proviso that when $R^6$ is benzylic in formula (XI) it is aliphatic in formula (XII), or vice versa, and selectively de-esterifying.

Compounds of general formula (XI) can simply be derived from amino acids, which can be obtained in enantiomerically pure form, enabling a choice of optically active compounds of formula (I) to be prepared.

Compounds of formula (II) and (IIA) are valuable intermediates in the preparation of compounds of formula (I), and in that respect form part of the present invention.

As mentioned above, compounds of formula (I) are useful in human or veterinary medicine since they are active as inhibitors of TNF and MMPs. Accordingly in another aspect, this invention concerns:

(i) a method of management (by which is meant treatment or prophylaxis) of diseases or conditions mediated by TNF and/or MMPs in mammals, in particular in humans, which method comprises administering to the mammal an effective, amount of a compound of formula (I) above, or a pharmaceutically acceptable salt thereof; and (ii) a compound of formula (I) for use in human or veterinary medicine, particularly in the management (by which is meant treatment or prophylaxis) of diseases or conditions mediated by TNF and/or MMPs; and (iii) the use of a compound of formula (I) in the preparation of an agent for the management (by which is meant treatment or prophylaxis) of diseases or conditions mediated by TNF and/or MMPs.

The diseases or conditions referred to above include inflammation, fever, cardiovascular effects, haemorrhage, coagulation and acute phase response, cachexia and anorexia, acute infections, shock states, graft versus host reactions autoimmune disease and inflammatory bowel disease (eg Crohn's disease); and those involving tissue breakdown such as bone resorption, inflammatory diseases, dermatological conditions, tumour growth, angiogenesis and invasion by secondary metastases, in particular rheumatoid arthritis, osteoarthritis, periodontitis, gingivitis, corneal ulceration, tumour growth, angiogenesis and invasion by secondary metastases.

In a further aspect of the invention there is provided a pharmaceutical or veterinary composition comprising a compound of formula (I) together with a pharmaceutically or veterinarily acceptable excipient or carrier.

One or more compounds of general formula (I) may be present in the composition together with one or more excipient or carrier.

The compounds with which the invention is concerned may be prepared for administration by any route consistent with their physicochemical and pharmacokinetic properties. The compositions thus may be in the form of tablets, capsules, powders, granules, lozenges, liquid or gel preparations, such as oral, topical, or sterile parenteral solutions or suspensions, as appropriate. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions. solutions, emulsions, syrups or elixirs, or may be presented as a dry product for reconstitution with water or other suitable vehicle before use. Such liquid preparations may contain conventional additives such as suspending agents, for example sorbitol. syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit for oral administration may contain from about 1 to 250 mg, for example from about 25 to 250 mg of a compound of general formula I. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle. For use in the treatment of rheumatoid arthritis, the drug can be administered by the oral route or by injection intra-articularly into the affected joint. The daily dosage for a 70 kg mammal may be in the range 10 mgs to 1 gram.

The examples 1–6 which follow serve to illustrate the invention but are not intended to limit the scope in any way. The amino acids used in these examples were commercially available or were prepared according to literature procedures. Biological Examples A–C illustrate the activity of some of the compounds of the invention.

The following abbreviations have been used throughout:

| | |
|---|---|
| DMF | N,N-Dimethylformamide |
| WSC | N-Ethyl-N'-(3-dimethylaminopropyl)carbodiimide hydrochloride |
| NMM | N-Methylmorpholine |
| HOBt | 1-Hydroxybenzotriazole |
| DCM | Dichloromethane |
| TFA | Trifluoroacetic acid |
| TLC | Thin layer chromatography |
| HPLC | High performance liquid chromatography |

$^1$H and $^{13}$C NMR spectra were recorded using a Bruker AC 250E spectrometer at 250.1 and 62.9 MHz, respectively. Elemental microanalyses were performed by CHN Analysis Ltd., Alpha House, Countesthorpe Road, South Wigston, Leicester LE8 2PJ, UK. HPLC was performed using a Beckman System Gold, and preparative HPLC using a Waters system.

EXAMPLE 1

$N^2$-[4-(N-Hydroxyamino)-3S-(4-hydroxyphenylthiomethyl)-2R-isobutylsuccinyl]-$N^6$-acetyl-L-lysine-$N^1$-methylamide

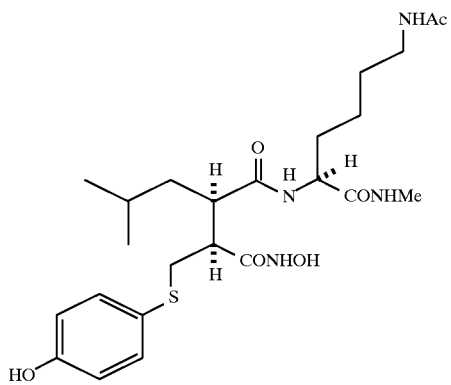

EXAMPLE 1a $N^2$-Benzyloxycarbonyl-$N^6$-tert-butyloxycarbonyl-L-lysine-$N^1$-methylamide $N^2$-Benzyloxycarbonyl-$N^6$-tert-butyloxycarbonyl-L-lysine (25.1 g, 66.1 mmol) and pentafluorophenol (15.8 g, 85.9 mmol) were dissolved together in DCM (100 ml). The solution was stirred and cooled to 0° C. before the addition of WSC (15.2 g, 79.3 mmol). The reaction mixture was allowed to warm to room temperature over 2 hours then cooled back to 0° C. during the addition of a solution of methylamine (8.03M) in ethanol (20.6 ml, 165.2 mmol). The solution was again allowed to warm to room temperature and stirred for a further 3 hours, then washed with 1M hydrochloric acid (2×100 ml), 1M sodium carbonate (2×100 ml) and brine (100 ml). The organic layer was dried over anhydrous magnesium sulphate, filtered and evaporated. The product was obtained by recrystallisation from ethyl acetate-hexane. Yield: 23.8 g (88%). $^1$H-NMR; δ (Chloroform-d): 7.31 (5H, m), 6.46 (1H, br m), 5.70 (1H, d, J=6.5 Hz), 5.07 (2H, m), 4.71 (1H, m), 4.13 (1H, m), 3.06 (2H, br m), 2.75 (3H, d, J=4.7 Hz), 1.91–1.22 (6H, br m) and 1.37 (9H, s).

EXAMPLE 1b $N^2$-Benzyloxycarbonyl-L-lysine-$N^1$-methylamide (Trifluoroacetate Salt)

$N^2$-Benzyloxycarbonyl-$N^6$-tert-butyloxycarbonyl-L-lysine-$N^1$-methylamide (23.7 g, 58.2 mmol) was dissolved in a mixture of DCM (35 ml) and TFA (35 ml) and stored at 0° C. overnight. The solvents were removed in vacuo and the residue was triturated with diethyl ether to produce a white solid which was collected by filtration. Yield: 31.2 g (ca. quant., assuming excess TFA present). $^1$H-NMR; δ (Dimethyl sulphoxide-$d_6$): 7.96–7.65 (4H, br m), 7.31 (5H, m), 5.01 (2H, m), 3.90 (1H, m), 2.75 (2H, m), 2.49 (3H, d, J=4.7 Hz) and 1.75–1.29 (6H, br m).

EXAMPLE 1c $N^2$-Benzyloxycarbonyl-$N^6$-acetyl-L-lysine-$N^1$-methylamide

The product from Example 1b (29.72 g 57.0 mmol) was suspended in DCM (500 ml) and the mixture was cooled in an ice bath. Acetic anhydride (6.4 g , 62.7 mmol), 4-dimethylaminopyridine (100 mg, catalytic) and triethylamine (17.9 g, 176.7 mmol) were added successively, with stirring to produce a homogeneous solution. The product began to crystallise after about 5 minutes. The reaction mixture was stirred for 1 hour at 0° C., then filtered. The solid was resuspended in water (500 ml) and stirred briefly, filtered, washed with more water then dried under high vacuum. Yield: 15.3 g (80%). $^1$H-NMR; δ (Methanol-$d_4$): 7.30 (5H, m), 5.02 (2H, m), 3.99 (1H, m), 3.13 (2H, m), 2.66 (3H, s), 1.88 (3H, s) and 1.78–1.22 (6H, br m).

EXAMPLE 1d $N^6$-Acetyl-L-lysine-$N^1$-methylamide $N^2$-benzyloxycarbonyl-$N^6$-acetyl-L-lysine-$N^1$-methylamide (15.26 g, 45.6 mmol) was suspended in ethanol (400 ml) and 10% palladium on charcoal (2.5 g) was added as a slurry in ethyl acetate. Hydrogen was passed through the solution for 40 minutes, after which time the starting material had all dissolved and TLC indicated complete conversion to a more polar product. The catalyst was filtered off and the solvent was removed to afford the title compound as a white solid. Yield: 9.79 g (ca. quant.). $^1$H-NMR; δ (Dimethyl sulphoxide-$d_6$): 7.77 (2H, m), 3.07 (1H, m), 2.98 (2H, m), 2.58 (3H, d, J=4.6 Hz), 2.32–2.04 (2H, br s), 1.77 (3H, s) and 1.61–1.16 (6H, br m).

EXAMPLE 1e

4-Benzyloxy-3-benzyloxycarbonyl-2R-isobutyl-1-pentafluorophenyl Succinate

4-Benzyloxy-3-benzyloxycarbonyl-2-R,S-isobutylsuccinic acid (ca. 85% R isomer) (97.15 g, 244 mmol), prepared according to the methods described in U.S. Pat. No. 5,241,958, was dissolved in DCM (400 ml) and the solution was cooled in an ice bath. Pentafluorophenol (53.86 g, 293 mmol) was added, followed by WSC (56.10 g, 293 mmol) and the reaction mixture was stirred at 0° C. for 1 hour and then at room temperature overnight. The solution was diluted with DCM (200 ml) and washed with 1M sodium carbonate (2×300 ml), 1M hydrochloric acid (2×300 ml) and brine (300 ml). The organic layer was dried over anhydrous magnesium sulphate, filtered, and evaporated to an oil which was further purified by column chromatography on silica (20% diethyl ether in hexane as eluent). Yield: 105.1 g (76%). $^1$H-NMR; δ (Chloroform-d): 7.33 (10H, m), 5.19 (4H, m), 3.95 (1H, d, J=10.1 Hz), 3.53 (1H, dt, J=10.1, 4.0 Hz). 1.74 (2H, m). 1.30 (1H, m), 0.92 (6H, 2d, J=5.6 Hz).

EXAMPLE 1f $N^2$-[4-Benzyloxy-3-benzyloxycarbonyl-2R,S-isobutylsuccinyl]-$N^6$-acetyl-L-lysine-$N^1$-methylamide The product from Example 1e (38.5 g. 63.2 mmol) and $N^6$-acetyl-L-lysine-$N^1$-methylamide (9.15 g, 45.5 mmol) were stirred together in DMF (100 ml) for 2 days at room temperature. The solvent was removed under reduced pressure, the residue dissolved in DCM (200 ml) and the solution washed with 1M sodium carbonate solution (2×200 ml) and brine (200 mL), dried over magnesium sulphate, filtered and evaporated. The residue was purified by column chromatography (gradient elution with 0–10% methanol in DCM) to afford first excess pentafluorophenyl ester followed by the title compound as a solid (26.6 g, diastereoisomer ratio 5:1, RS:SS by $^1$H NMR). Recrystallisation from ethyl acetate-hexane gave a slight increase in diastereoisomer ratio (6:1). Yield: 16.08 9 (63%). $^1$H-NMR; δ (Chloroform-d, major diastereoisomer): 7.35–7.15 (10H, br m), 7.13 (1H, d, J=7.4 Hz), 6.78 (1H, m), 6.23 (1H, m), 5.22–4.99 (4H, br m), 4.28 (1H, m), 3.83 (1H, d, J=10.2 Hz), 3.28 (1H, m), 3.05 (2H, m), 2.72 (3H, d, J=4.7 Hz), 1.87 (3H, s), 1.85–1.18 (8H, br m). 1.05 (1H, m), 0.83 (3H, d, J=6.4 Hz) and 0.79 (3H, d, J=6.4 Hz).

EXAMPLE 1g $N^2$-[4-Hydroxy-2R-isobutyl-3-methylenesuccinyl)]-$N^6$-acetyl-L-lysine-$N^1$-methylamide The product from Example 1f (16.0 g, 28.4 mmol) was dissolved in ethanol (250 ml) and subjected to catalytic hydrogenolysis, as described in Example 1d. After 1 hour no starting material remained (TLC) so the catalyst was removed by filtration and the solvent was evaporated to leave an oil (12.0 g). $^1$H NMR confirmed the presence of the dicarboxylic acid along with solvent.

The crude dicarboxylic acid (9.71 g, ca. 25 mmol) was redissolved in ethanol (150 ml) and piperidine (2.36 g, 27.7 mmol) was added. The mixture was cooled in an ice bath and treated with 37% formaldehyde solution (19 ml, 252 mmol), then allowed to warm to room temperature overnight. The solvents were removed in vacuo and the residue was purified by column chromatography, using DCM-methanol-acetic acid (90:9:1) as eluent, to give the title compound as a white foam. Yield: 5.35 g (60%), single diastereoisomer. $^1$H-NMR; δ (Methanol-$d_4$): 6.31 (1H, s), 5.78 (1H, s), 4.22 (1H, dd, J=5.4, 8.8 Hz), 3.58 (1H, m), 3.09 (2H, t, J=6.8 Hz), 2.69 (3H, s), 1.88 (3H, s), 1.78–1.18 (9H, br m), 0.90 (3H, d, J=6.2 Hz) and 0.86 (3H, d, J=6.3 Hz).

EXAMPLE 1h $N^2$-[4-Hydroxy-3S-(4-hydroxyphenylthiomethyl)-2R-isobutylsuccinyl]-$N^6$-acetyl-L-lysine-$N^1$-methylamide $N^2$-[4-Hydroxy-2R-isobutyl-3-methylenesuccinyl]-$N^6$-acetyl-L-lysine-$N^1$-methylamide (5.11 g, 14.5 mmol), 4-hydroxythiophenol (25 ml) and triethylamine (1.0 ml, 7.3 mmol) were dissolved in methanol (50 ml) under argon. The mixture was heated at 60° C. in the dark for 2 days. Solvents were removed under reduced pressure and the residual oil was purified by column chromatography (gradient elution with 0–30 % methanol in DCM). Yield 3.91 g (55%). $^1$H-NMR; δ (Dimethyl sulphoxide-$d_6$,): 8.18 (1H, d, J=7.3 Hz), 7.76 (2H, m), 7.15 (2H, d, J=8.5 Hz), 6.71 (2H, d, J=8.5 Hz), 4.15 (1H, m), 2.99 (2H, m), 2.79 (1H, m), 2.55 (3H, d, J=4.5 Hz), 2.89–2.54 (3H, m), 1.79 (3H, s), 1.60–1.06 (8H, br m), 0.94 (1H, m), 0.80 (3H, d, J=6.4 Hz) and 0.75 (3H, d, J=6.5 Hz).

EXAMPLE 1i $N^2$-[4-(N-Hydroxyamino)-3S-(4-hydroxyphenylthiomethyl)-2R-isobutylsuccinyl]-$N^6$-acetyl-L-lysine-$N^1$-methylamide To a cooled (0° C.) solution of ($N^2$-[4-hydroxy-3S-(4-hydroxyphenylthiomethyl)-2R-isobutylsuccinyl)]-$N^6$-acetyl-L-lysine-$N^1$-methylamide (3.90 g, 7.86 mmol) in DMF (70 ml) was added successively HOBt (1.27 g, 9.4 mmol) and WSC (1.81 g, 9.4 mmol). The solution was allowed to warm to room temperature over 2 hours, hydroxylamine hydrochloride (0.81 g, 11.8 mmol) and NMM (1.19 g, 11.8 mmol) were added and the reaction mixture was stirred for two days. The solvent was removed and the product was purified by column chromatography on acid-washed silica (gradient elution with 0–20% methanol in DCM). followed by recrystallisation from aqueous methanol. Yield: 1.36 g (34%), in three crops. $^1$H-NMR; δ (Dimethyl sulphoxide-$d_6$): 10.60 (1H, s), 9.50 (1H, s), 8.90 (1H, s), 8.15 (1H, d, J=7.9 Hz), 7.83–7.63 (2H, br m), 7.10 (2H, d, J=8.4 Hz), 6.69 (2H, d, J=8.4 Hz), 4.12 (1H, m), 3.04–2.82 (3H, br m), 2.62 (1H, m), 2.88–2.48 (1H, br m), 2.54 (3H, d, J=4.2 Hz), 2.27 (1H, m), 1.78 (3H, s), 1.60–1.03 (8H, br m), 0.90 (1H, m), 0.79 (3H, d, J=6.3 Hz) and 0.75 (3H, d, J=6.4 Hz). $^{13}$C-NMR; δ (Dimethyl sulphoxide-$d_6$): 172.7, 171.8, 169.0, 168.2, 156.5, 132.0, 124.2, 116.1, 52.4, 46.2, 46.1, 38.3, 36.0, 31.4, 28.7, 25.4, 25.1, 24.0, 22.9, 22.6 and 21.4. Found: C, 55.86, H, 7.39, N, 10.95%; $C_{24}H_{38}N_4O_6S.0.3\ H_2O$ requires: C, 55.86, H, 7.54, N, 10.86%.

EXAMPLE 2

$N^2$-[4-(N-Hydroxyamino)-3S-(4-hydroxyphenylthiomethyl)-2R-isobutylsuccinyl]-$N^6$-tert-butyloxycarbonyl-L-lysine-$N^1$-methylamide

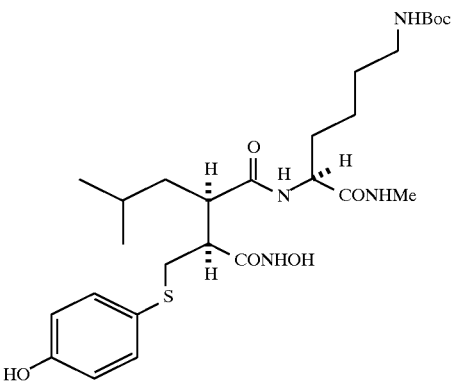

EXAMPLE 2a $N^6$-tert-Butyloxycarbonyl-L-lysine-$N^1$-methylamide $N^2$-Benzyloxycarbonyl-$N^6$-tert-butyloxycarbonyl-L-lysine-$N^1$-methylamide (26.5 g, 69.3 mmol), prepared by the method described in Example 1a, was dissolved in ethanol (360 ml) and cyclohexene (40 ml). 10% Palladium on charcoal (3 g) was added as a slurry in ethyl acetate and the mixture was stirred and heated under reflux for 40 minutes. TLC indicated a single product (ninhydrin positive). The catalyst was removed by filtration and the filtrate was evaporated to dryness to afford an oil (19.54 g, residual solvent present) which was used in Example 2b without further purification. $^1$H-NMR; δ (Methanol-d$_4$): 3.23 (1H, t, J=6.5 Hz), 2.98 (2H, t, J=6.8 Hz), 2.67 (3H, s), 1.64–1.20 (6H, br m) and 1.29 (9H, s).

EXAMPLE 2b $N^2$-[4-Benzyloxy-3-benzyloxycarbonyl-2R-isobutylsuccinyl]-$N^6$-tert-butyloxycarbonyl-L-lysine-$N^1$-methylamide By a method analogous to that described in Example 1f, $N^6$-tert-butyloxycarbonyl-L-lysine-$N^1$-methylamide (17.14 g, 69.3 mmol) was converted to the title compound. The crude product was purified by column chromatography on silica (gradient elution with 0–5% methanol in DCM). Yield: 37.36 g (86%), 9:1 mixture of diastereoisomers (RS:SS). $^1$H-NMR; δ (Chloroform-d, major diastereoisomer): 7.35–7.17 (10H, br m), 6.68 (1H, d, J=7.9 Hz), 6.47 (1H, m), 5.20–5.01 (4H, br m), 4.79 (1H, m), 4.32 (1H, m), 3.82 (1H, d, J=9.8 Hz), 3.05 (2H, m), 2.95 (1H, m), 2.75 (3H, d, J=4.8 Hz), 1.89–1.24 (9H, br m), 1.40 (9H, s), 0.81 (3H, d, J=5.1 Hz) and 0.78 (3H, d, J=5.1 Hz).

EXAMPLE 2c $N^2$-[4-Hydroxy-2R-isobutyl-3-methylenesuccinyl]-$N^6$-tert-butyloxycarbonyl-L-lysine-$N^1$-methylamide $N^2$-[4-Benzyloxy-3-benzyloxycarbonyl-2R-isobutylsuccinyl]-$N^6$-tert-butyloxycarbonyl-L-lysine-$N^1$-methylamide (37.36 g, 59.5 mmol) was dissolved in ethanol and subjected to catalytic hydrogenolysis, as described in Example 1d. The resulting dicarboxylic acid was dissolved in ethanol (250 ml) and piperidine (5.25 g, 62.1 mmol), the solution was cooled to 0° C. and 37% formaldehyde solution (42.3 ml, 564 mmol) was added dropwise. The reaction mixture was allowed to warm to room temperature overnight. The solvents were removed in vacuo, leaving an oil which was dissolved in ethyl acetate (800 ml) and washed with 1M hydrochloric acid (2×100 ml) and brine (100 ml). The organic layer was dried over anhydrous sodium sulphate, filtered and evaporated to a viscous oil (18.20 g, 78%), which contained the title compound along with an unidentified impurity. $^1$H-NMR; δ (Methanol-d$_4$): 6.31 (1H, s), 5.78 (1H, s), 4.22 (1H, m), 3.58 (1H, m), 3.21 (2H, m), 2.68 (3H, d, J=4.5 Hz), 1.91–1.09 (9H, br m), 1.43 (9H, s), 0.90 (3H, d, J=6.3 Hz) and 0.86 (3H, d, J=6.3 Hz).

EXAMPLE 2d $N^2$-[4-Hydroxy-3S-(4-hydroxyphenylthiomethyl)-2R-isobutylsuccinyl]-$N^6$-tert-butyloxycarbonyl-L-lysine-$N^1$-methylamide By a method analogous to that described in Example 1h, the product from Example 2c (18.20 g, 43.8 mmol) was converted to a mixture of products. Excess thiol was removed by column chromatography on silica (gradient elution with 2–10% methanol in DCM) to give an inseparable mixture of the title compound and an unidentified impurity . Yield: 9.45 g (40 %). $^1$H-NMR; δ (Methanol-d$_4$): 7.21 (2H, d), 6.68 (2H, d), 4.23 (1H, m), 3.24 (3H, m), 2.95 (1H, m), 2.83–2.48 (5H, s and m), 1.79 –1.03 (9H, br m), 0.84 (3H, d, J=6.3 Hz) and 0.79 (3H, d. J=6.3 Hz).

EXAMPLE 2e $N^2$-[4-(N-Hydroxyamino)-3S-(4-hydroxyphenylthiomethyl)-2R-isobutylsuccinyl]-$N^6$-tert-butyloxycarbonyl-L-lysine-$N^1$-methylamide The product from Example 2d (6.48 g) in DMF (70 ml) was cooled in an ice bath and HOBt (2.08 g, 15.4 mmol), WSC (2.95 g, 15.4 mmol) and N-methylmorpholine (1.56 g, 15.4 mmol) were added successively. The reaction mixture was allowed to warm to room temperature over two hours. Hydroxylamine hydrochloride (1.64 g, 23.7 mmol) and NMM (2.39 g, 23.7 mmol) were added and the mixture was stirred overnight. The solvent was removed and the product was partially purified by column chromatography on acid washed silica (gradient elution with 2–5% methanol in DCM) to give 0.95 g of a while foam which contained two major components (HPLC). A 250 mg sample of the recovered material was separated by preparative reverse phase HPLC (Waters, Delta Pak C18-300 A, gradient elution with 10–50% (80% acetonitrile/water) In 0.1% TFA/water). Fractions were neutralised by dropwise addition of 0.1M sodium hydroxide before evaporation to give the title compound (ca. 100 mg) as a white solid. $^1$H-NMR; δ (Methanol-d$_4$): 7.11 (2H, d, J=8.5 Hz), 6.59 (2H, d, J=8.5 Hz), 4.21 (1H, m), 2.94 (3H, m), 2.68 (1H, m), 2.67 (3H, s), 2.52 (1H, m), 2.32 (1H, m), 1.72–1.16 (8H, br m), 1.40 (9H, s), 1.07 (1H, m), 0.83 (3H, d, J=6.4 Hz) and 0.78 (3H, d, J=6.5 Hz). $^{13}$C-NMR; δ (Methanol-d$_4$): 176.3, 174.5, 168.6, 163.3, 158.5, 134.9, 122.3, 118.9, 79.8, 54.7, 48.2, 48.0, 41.3, 41.0, 38.5, 32.6, 30.4, 28.8, 26.9, 26.2, 24.3, 21.8.

EXAMPLE 3

$N^2$-[4-(N-Hydroxyamino)-3S-(4-hydroxyphenylthiomethyl)-2R-isobutylsuccinyl]-$N^6$-tert-butyloxycarbonyl-$N^6$-(4-hydroxyphenylthiomethyl)-L-lysine-$N^1$-methylamide

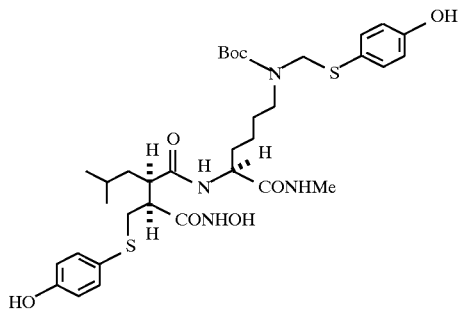

By the preparative HPLC method described in Example 2e, was also obtained the title compound (ca. 150 mg) as a white solid. $^1$H-NMR; δ (Methanol-d$_4$): 7.15 (4H, m), 6.65 (4H, m), 4.50 (2H, s), 4.21 (1H, m), 3.21 (2H, m), 2.94 (1H, m), 2.71 (1H, m), 2.67 (3H, s), 2.55 (1H, m), 2.34 (1H, m), 1.75–1.13 (8H, br m), 1.19 (9H, s), 1.05 (1H, m), 0.83 (3H, d, J=6.4 Hz) and 0.79 (3H, d, J=6.5 Hz). $^{13}$C-NMR; δ (Methanol-d$_4$); 176.1, 174.4, 169.5, 162.8, 160.4, 156.6, 137.8, 137.1, 134.5, 124.3, 118.3, 117.9, 81.4, 54.7, 48.2, 48.1, 46.0, 41.4, 37.9, 32.7, 28.7, 28.4, 28.2, 26.9, 26.3, 24.4, 24.4 and 21.8.

EXAMPLE 4

N$^2$-[4-(N-Hydroxyamino)-3S-(2-thienythiomethyl)-2R-isobutylsuccinyl]-N$^6$-tert-butyloxycarbonyl-L-lysine-N$^1$-methylamide

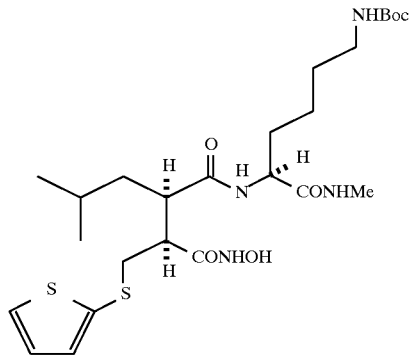

EXAMPLE 4a

N$^2$-[4-Hydroxy-3S-(2-thienylthiomethyl)-2R-isobutylsuccinyl]-N$^6$-tert-butyloxycarbonyl-L-lysine-N$^1$-methylamide N$^2$-[-4-Hydroxy-2R-isobutyl-3-methylenesuccinyl]-N$^6$-tert-butyloxycarbonyl-L-lysine-N$^1$-methylamide (4.0 g, 9.6 mmol) was dissolved in methanol (20 ml), thiophene-2-thiol was added and the mixture was stirred overnight under an argon and in the dark at 60° C. The solvent was removed under reduced pressure and the residual oil was purified by column chromatography on silica (0–10% methanol in DCM as eluent) to give the required product contaminated with a minor impurity. Yield: 0.93 g. $^1$H-NMR; δ (Methanol-d$_4$): 7.38 (1H, m), 7.09 (1H, m), 6.90 (1H, m), 4.20 (1H, m), 3.25 (2H, m), 2.97 (1H, m), 2.75 (1H, m), 2.67 (3H, s), 2.65 (2H, m), 1.75–1.02 (9H, br m), 1.21 (9H, s), 0.85 (3H, s, J=6.5 Hz) and 0.81 (3H, s, J=6.5 Hz).

EXAMPLE 4b

N$^2$-[4-(N-Hydroxyamino)-3S-(2-thienythiomethyl)-2R-isobutylsuccinyl]-N$^6$-tert-butyloxycarbonyl-L-lysine-N$^1$-methylamide N$^2$-[4-Hydroxy-3S-(2-thienythiomethyl)-2R-isobutylsuccinyl]-N$^6$-tert-butyloxycarbonyl-L-lysine-N$^1$-methylamide (0.91 g, 1.71 mmol) was dissolved in DMF (10 ml) and the solution was cooled in an ice bath during the addition of HOBt (0.30 g, 2.22 mmol), NMM (0.22 g, 2.22 mmol) and WSC (0.43 g, 2.22 mmol). The mixture was allowed to warm to room temperature and stirred for 2 hours. Hydroxylamine hydrochloride (0.24 g, 3.42 mmol) and NMM (0.35 g, 3.42 mmol) were added and the mixture was stirred overnight. The solvent was removed under reduced pressure to leave an oil which was purified by column chromatography on acid washed silica using 5% methanol in DCM as eluent) to give the required product contaminated with a small amount of an unknown impurity. Yield: ca. 200 mg. $^1$H-NMR; δ (Methanol-d$_4$): 7.39 (1H, m), 7.09 (1H, m), 6.93 (1H, m), 4.21 (1H, m), 3.25 (2H, m), 2.97 (1H, m), 2.73 (1H, m), 2.66 (3H, s), 2.56 (1H, m), 2.40 (1H, m), 1.74–1.12 (8H, br m), 1.21 (9H, s), 1.03 (1H, m), 0.84 (3H, d, J=6.4 Hz) and 0.80 (3H, d, J=6.5 Hz). $^{13}$C-NMR; δ (Methanol-d$_4$): 176.1, 174.3, 172.4, 172.0, 134.5, 131.1, 128.7, 82.3, 57.5, 54.5, 46.4, 41.5, 41.0, 33.0, 29.1, 28.3, 28.6, 27.2, 26.8, 24.3, 24.2 and 22.1.

EXAMPLE 5

N$^2$-[4-(N-Hydroxyamino)-3S-(4-hydroxyphenylthiomethyl)-2R-isobutylsuccinyl]-O-tert-butyl-L-threonine-N$^1$-methylamide

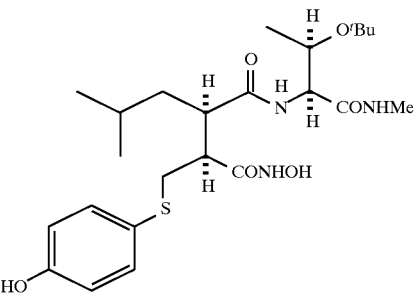

The title compound was prepared in a manner analogous to that described in Example 1, from N-benzyloxycarbonyl-O-tert-butyl-L-threonine. $^1$H-NMR; δ (Methanol-d$_4$): 7.18 (2H, d, J=8.5 Hz), 6.67 (2H, d, J=8.5 Hz), 4.35 (1H, d, J=3.6 Hz), 3.90 (1H, m), 3.01 (1H, m), 2.59–2.78 (2H, br m), 2.71 (3H, s), 2.38 (1H, dt, J=3.3, 11.0 Hz), 1.50 (1H, m), 1.36 (1H, m), 1.17 (9H, s), 1.09 (1H, m), 1.03 (3H, d, J=6.4 Hz), 0.86 (3H, d, J=6.4 Hz) and 0.80 (3H, d, J=6.5 Hz). $^{13}$C-NMR; δ (Methanol-d$_4$): 175.3, 171.9, 171.3, 158.3, 134.5, 125.8, 117.1, 76.0, 68.6, 59.4, 50.0–48.0 (1 s under solvent peak), 41.3, 37.9, 28.5, 27.0, 26.2, 24.3, 21.8 and 19.4.

EXAMPLE 6

N$^2$-[4-(N-Hydroxyamino)-3S-(4-hydroxyphenylthiomethyl)-2R-isobutylsuccinyl]-L-glutamine-N$^1$,N$^5$-dimethylamide

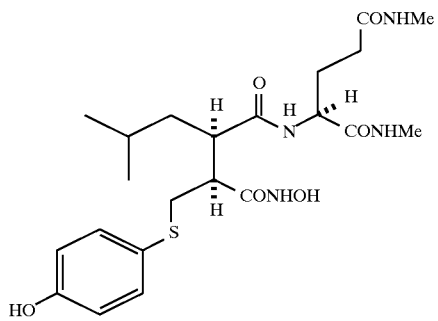

The title compound was prepared in a manner analogous to that described in Example 1, from N-tert-butyloxycarbonyl-L-glutamic acid. $^1$H-NMR; δ (Methanol-d$_4$): 7.10 (2H, d, J=8.7 Hz), 6.69 (2H, d, 8.7 Hz), 4.25 (1H, dd, J=6.2, 6.8 Hz), 3.05–2.76 (2H, m), 2.70 (6H, 2s), 2.57 (1H, dt, J=5.0, 9.4 Hz), 2.35 (1H, dt, J=5.0, 9.4 Hz), 2.19 (2H, t, J=6.9 Hz), 1.60–1.25 (2H, m), 1.10–0.95 (2H, m) and 0.82 (3H, d, J=6.3 Hz) and 0.80 (3H, d, J=6.3 Hz). $^{13}$C-NMR; δ (Methanol-d$_4$): 175.8, 175.3, 173.9, 171.4, 158.3, 134.4, 125.7, 117.1, 54.2, 41.4, 37.2, 33.0, 28.9, 26.8, 26.4, 26.2, 24.2 and 21.3.

EXAMPLE 7 (BB-3231)

N²-[4-(N-Hydroxyamino)-3S-(4-hydroxyphenylsulphonylmethyl-2R-isobutylsuccinyl)]-N⁶-acetyl-L-lysine-N¹-methylamide

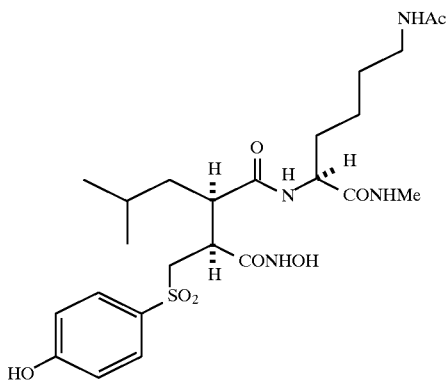

The product from Example 1 (167 mg, 0.33 mmol) was dissolved in methanol (5 ml) and cooled to 0° C. in an ice bath. m-Chloroperbenzoic acid (124 mg, 0.72 mmol) was added and the mixture was allow to warm to room temperature and stirred for 4 hours. The solvent was removed under reduced pressure and the residue was triturated with diethyl ether, filtered, washed with diethyl ether and dried under vacuum to afford a white solid (160 mg, 89%). $^1$H-NMR; δ (Dimethyl sulphoxide-d$_6$, 330 K): 10.45 (1H, br s), 7.72 (1H, m), 7.47 (2H, d, J=8.7 Hz), 7.33 (2H, m), 6.78 (2H, d, J=8.7 Hz), 3.96 (1H, m), 2.87 (3H, m), 2.42 (3H, d, J=4.6 Hz), 2.37 (1H, m), 1.66 (3H, s), 1.43–0.82 (11H, br m) and 0.63 (6H, m). $^{13}$C-NMR; δ (Dimethyl sulphoxide-d$_6$): 170.3, 170.1, 167.7, 165.5, 160.9, 128.9, 128.6, 114.5, 63.6, 61.9, 54.8, 51.2, 44.4, 30.0, 27.4, 24.1, 23.7, 22.6, 21.6, 21.3, 20.3 and 20.1. IR $v_{max}$ (Kbr disk) 3291, 2932, 1635, 1583, 1543, 1448, 1412, 1372, 1295 and 1140 cm$^{-1}$. Found: C, 51.41, H, 7.03, N, 9.79%; $C_{24}H_{38}N_4O_8S.H_2O$ requires: C, 51.41, H, 7.19, N, 9.99%.

BIOLOGICAL EXAMPLE A

The ability of example compounds of the invention to inhibit the release of TNF was investigated. The assay is based on the ability of phorbol myristate acetate (PMA) to stimulate the release of TNF a from a human monocytic cell line, U937.

U937 cells cultured in RPMI 1640 medium+5% foetal calf serum are centifuged at 1000×g for 5 minutes and then resuspended in medium at 2×10⁶/ml. 1 ml of cell suspension is aliquoted into individual wells of 24-well plates. Test compounds are dissolved in dimethyl sulphoxide (DMSO) at a stock concentration of 100 mM, then diluted to 50× the final required concentration with RPMI 1640 medium. 20 μl of the diluted compounds are added to U937 cells in duplicate wells. TNF a release is stimulated by addition of PMA to the cells at a final concentration of 50 nM. Appropriate control cultures are set up in duplicate. The plates are incubated for 18 hours at 37° C., 5% $CO_2$, then centrifuged at 1000×g for 5 minutes. A specific ELISA for TNFα obtained from British Bio-technology Products Limited, Abingdon, England is used to measure TNFα levels in the culture supernatants The average concentration of test compound which inhibits the release of TNF a by 50% relative to the control culture was assessed. The compounds of examples 1, 2, 3, 4 and 6 above were tested and had IC$_{50}$ values less than 50 μM.

BIOLOGICAL EXAMPLE B

The compound of Example 1 was assessed for its ability to inhibit release of endotoxin induced TNF production in vivo.

Male Male CD rats (Charles River, UK) weighing between 300 g–400 g were anaesthetised with an intraperitoneal injection of a mixture of 62.5 mg·kg$^{-1}$ thiopental and 22.5 mg·kg$^{-1}$ sodium pentobarbitone (Thiopental, Sigma Chemical Co., UK; Sodium pentobarbitone (Sagatal), May and Baker., UK). The trachea was exposed and cannulated to allow spontaneous respiration through a patent airway. The left jugular vein was exposed and cannulated for the administration of LPS. The right femoral artery was exposed and cannulated for withdrawal of blood samples.

Blood samples (1 ml) were removed just prior to bolus administration of either LPS (E. coli serotype 0111:b$_4$, Difco Laboratories, USA) or saline (NaCL 0.9% w/v) and at intervals of 1 hour and 2 hours after LPS. Removed blood was replaced with equal amounts of saline.

Rats were administered LPS at a dose of 50 μg·kg$^{-1}$ which resulted in a marked increase in TNF a levels in comparison to saline controls. The peak of TNF release was at the 1 hour timepoint. THF levels were expressed in units/ml where 1 unit is the equivalent of 1 pg of mouse TNFα.

Rat serum TNF levels were measured using a mouse TNFα reference standard. The commercial ELISA kits were from Genzyme.

The compound of example 1 was administered intravenously to aneasthetised rats at a dose of 10 mg·kg$^{-1}$, 15 minutes prior to LPS administration. The infusion was maintained for the 2 hour duration of the experiment. The compound of example 1 reduced the LPS-induced release of TNF by more than 50% at both the 1 and 2 hour timepoints.

BIOLOGICAL EXAMPLE C

The potency of compounds of Examples 1 to 6 to act as inhibitors of collagenase was determined by the procedure of Cawston and Barrett, (Anal. Biochem., 99, 340–345, 1979), hereby incorporated by reference, whereby a 1 mM solution of the compound being tested, or a dilution thereof, was incubated at 37° for 16 hours with collagen and collagenase (buffered with 25 mM Hepes, pH 7.5 containing 5 mM $CaCl_2$, 0.05% Brij 35 and 0.02% NaN$_3$). The collagen was acetylated $^{14}$C collagen prepared by the method of Cawston and Murphy, (Methods in Enzymology, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity (IC$_{50}$).

The potency of compounds of Examples 1 to 6 to act as inhibitors of stromelysin was determined by the procedure of Cawston et al, (Biochem. J., 195, 159–165, 1981), hereby incorporated by reference, whereby a 1 mM solution of the compound being tested, or a dilution thereof, was incubated at 37° for 16 hours with stromelysin and $^{14}$C acetylate casein (buffered with 25 mM Hepes, pH 7.5 containing 5 mM $CaCl_2$, 0.05% Brij 35 and 0.02% NaN$_3$). The casein was acetylated $^{14}$C casein prepared by the method of Cawston et al (ibid). The stromelysin activity in the presence of 1 mM of the test compound, or a dilution thereof, was compared to activity in a control devoid of inhibitor and the result reported below as that of inhibitor concentration effecting 50% inhibition of the stromelysin activity (IC$_{50}$).

Results:

| Compound | Collagenase IC$_{50}$ | Stromelysin IC$_{50}$ |
|---|---|---|
| Example 1 | 5 | 30 |
| Example 2 | 15 | 15 |
| Example 3 | 30 | 50 |
| Example 4 | 10 | 20 |
| Example 5 | 5 | 40 |
| Example 6 | 6 | 70 |

We claim:

1. A compound of formula (I):

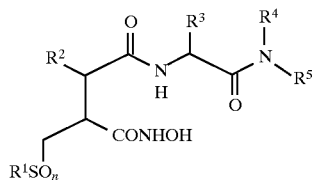

wherein:
$R^1$ is 4-methoxyphenyl, 4-hydroxyphenyl, 4-aminophenyl, or thien-2-yl;
$R^2$ represents a $(C_1-C_6)$alkyl group;
$R^3$ represents
  the side chain of lysine, in which the amino group is substituted by $(C_1-C_6\text{alkyl})OC(=O)-$, or $(C_1-C_6\text{alkyl})C(=O)-$;
$R^4$ represents hydrogen or a $(C_1-C_6)$alkyl or phenyl$(C_1-C_6)$alkyl group;
$R^5$ represents hydrogen or a methyl group; and
n is 0, 1 or 2;
or a salt solvate or hydrate thereof.

2. A compound as claimed in claim 1 wherein the chiral center adjacent of the substituent $R^3$ has S stereochemistry.

3. A compound as claimed in claim 2 wherein the chiral center adjacent to the substituent $R^2$ has R stereochemistry.

4. A compound as claimed in claim 3 wherein the chiral center adjacent to the —CONHOH moiety has S stereochemistry.

5. A compound as claimed in claim 4 wherein $R^2$ represents a $(C_3-C_6)$alkyl group.

6. A compound as claimed in claim 4 wherein $R^4$ represents a $(C_1-C_4)$alkyl group.

7. A compound as claimed in claim 4 wherein $R^5$ represents a hydrogen atom.

8. A compound as claimed in claim 4 wherein n=0 or 2.

9. A compound as claimed in claim 4 wherein:
$R^2$ represents a $(C_3-C_6)$alkyl group;
$R^4$ represents a $(C_1-C_4)$alkyl group;
$R^5$ represents a hydrogen atom; and
n=0 or 2.

10. A compound as claimed in claim 1, selected from the group consisting of:

$N^2$[4-(N-Hydroxyamino)-3S-(4-hydroxyphenylthiomethyl)-2R-isobutylsuccinyl]-$N^6$-tert-butyloxycarbonyl-L-lysine-$N^1$-methylamide,
$N^2$[4-(N-Hydroxyamino)-3S-(4-hydroxyphenylthiomethyl)-2R-isobutylsuccinyl]-$N^6$-tert-butyloxycarbonyl-$N^6$-(4-hydroxyphenylthiomethyl)-L-lysine-$N^1$-methylamide,
$N^2$[4-(N-hydroxyamino)-3S-(2-thienylthiomethyl)-2R-isobutylsuccinyl]-$N^6$-tert-butyloxycarbonyl-L-lysine-$N^1$-methylamide,
[$N^2$[4-(N-Hydroxyamino)-3S-(4-hydroxyphenylthiomethyl)-2R-isobutylsuccinyl]-O-tert-butyl-L-threonine-$N^1$-methylamide,
$N^2$[4-(N-Hydroxyamino)-3S-(4-hydroxyphenylthiomethyl)-2R-isobutylsuccinyl]-L-glutamine-$N^1$,$N^5$-dimethylamide,]
$N^2$[4-(N-Hydroxyamino)-3S-(4-hydroxyphenylsulphonylmethyl)-2R-isobutylsuccinyl]-$N^6$-acetyl-L-lysine-$N^1$-methylamide, and salts, hydrates and solvates thereof.

11. $N^2$-[4-(N-Hydroxyamino)-3S-(4-hydroxyphenylthiomethyl)-2R-isobutylsuccinyl]-$N^6$-acetyl-L-lysine-$N^1$-methylamide and salts, hydrates and solvates thereof.

12. A method of treatment of diseases or conditions mediated by TNF or MMPs in mammals, which method comprises administering to the mammal an effective amount of a compound as claimed in any one of claims 1 to 4, 5 to 7, 8 to 11.

13. A method as claimed in claim 12, wherein the disease or condition referred to is inflammation, fever, cardiovascular effects, hemorrhage, coagulation and acute phase response, cachexia or anorexia, acute infections, shock states, graft versus host reactions or autoimmune disease.

14. A method as claimed in claim 12, wherein the disease or condition referred to is rheumatoid arthritis, osteoarthritis, periodontitis, gingivitis, corneal ulceration, tumor growth, tumor angiogenisis or tumor invasion by secondary metastases.

15. A pharmaceutical or veterinary composition comprising an effective amount a compound as claimed in any one of claims 1 to 4, 5 to 7, 8 to 11 together with a pharmaceutically or veterinarily acceptable excipient or carrier.

* * * * *

UNITED STATES PATENT AND TRADEMARK OFFICE
CERTIFICATE OF CORRECTION

PATENT NO.: 5,821,262

DATED: October 13, 1998

INVENTOR(S): Michael John CRIMMIN et al.

It is certified that an error appears in the above-identified patent and that said Letters Patent is hereby corrected as shown below:

On the title page, item [57],
the Abstract, line 14 after the formula, after "or" insert --a methyl group;-- and
line 15 after the formula, delete "or substituted phenyl groups;".

Column 22, lines 15-20 (Claim 10, lines 12-17), delete in their entirety.

Signed and Sealed this

Nineteenth Day of January, 1999

Attest:

Attesting Officer

*Acting Commissioner of Patents and Trademarks*